(12) United States Patent
Mangold et al.

(10) Patent No.: US 7,696,111 B2
(45) Date of Patent: Apr. 13, 2010

(54) COSMETIC PAD (75) Inventors: Rainer Mangold, Herbrechtingen (DE);
 Angela Römpp, Zell u. A. (DE); Jana Michelmann, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 11/490,051

(22) Filed: Jul. 21, 2006

(65) Prior Publication Data
US 2006/0258250 A1 Nov. 16, 2006

Related U.S. Application Data (63) Continuation of application No. 10/514,312, filed as application No. PCT/EP03/07629 on Jul. 15, 2003, now abandoned.

(30) Foreign Application Priority Data

Jul. 15, 2002 (EP) .................................. 02400033

(51) Int. Cl.
 *B32B 27/02* (2006.01)
 *B32B 27/04* (2006.01)
 *B32B 23/02* (2006.01)
 *D04H 1/00* (2006.01)
 *D04H 1/58* (2006.01)
 *A61L 15/48* (2006.01)

(52) U.S. Cl. ........................ 442/344; 442/340; 442/351; 442/361; 442/362; 442/364; 442/408; 442/409; 442/411; 442/415; 442/416; 442/417; 442/123; 15/229.14; 604/365; 604/366; 604/367; 604/370; 604/374; 604/377

(58) Field of Classification Search ......... 442/340–341, 442/344–346, 350–351; 15/208, 209.1
See application file for complete search history.

(56) References Cited

U.S. PATENT DOCUMENTS

| 2,988,468 | A | * | 6/1961 | Strickel et al. ............... 442/341 |
| 4,307,143 | A | * | 12/1981 | Meitner ................... 15/104.93 |
| 4,426,417 | A | * | 1/1984 | Meitner et al. ........... 428/195.1 |
| 4,769,022 | A | | 9/1988 | Chang |
| 6,287,419 | B1 | * | 9/2001 | Takeuchi et al. ............. 162/115 |
| 6,342,208 | B1 | * | 1/2002 | Hyldgaard et al. ............ 424/59 |
| 6,737,004 | B2 | * | 5/2004 | Wang et al. ................. 264/103 |
| 6,808,598 | B1 | * | 10/2004 | Takeuchi et al. ............. 162/115 |
| 2002/0034907 | A1 | * | 3/2002 | Groitzsch et al. ........... 442/327 |
| 2002/0146956 | A1 | * | 10/2002 | Ngai .......................... 442/381 |

(Continued)

FOREIGN PATENT DOCUMENTS

EP 600844 A1 * 6/1994

(Continued)

OTHER PUBLICATIONS

"Product Details: Cotton Comber Noils". Behn Meyer Group, www.behnmeyer.com.*

(Continued)

*Primary Examiner*—Jennifer A Chriss
(74) *Attorney, Agent, or Firm*—Paul Vincent (57) ABSTRACT

The inventive cosmetic pad (2) exhibiting an improved effectiveness thereof for make-up removal contains or consists of discontinuous synthetic micro staple fibers whose length is equal to or greater than 7 mm.

24 Claims, 9 Drawing Sheets

U.S. PATENT DOCUMENTS

2004/0245139 A1 * 12/2004 Mangold et al. ............ 206/494
2005/0267395 A1 * 12/2005 Mangold et al. ............... 604/1

FOREIGN PATENT DOCUMENTS

WO    WO 2004007825 A2 *  1/2004

OTHER PUBLICATIONS

"Staple", Complete Textile Glossary by Celanese Acetate, 2001, 4 pages total.*

"Meltblowing", Complete Textile Glossary by Celanese Acetate, 2001, 3 pages.*

"Cosmetic", Federal Food, Drug and Cosmetic Act from FDA website, 6 pages.*

"Spunlaced Fabrics", Developments in Non-Woven Fabrics, The Textile Institute, vol. 12, No. 4, 1983, 4 pages.*

Parikh, D.V. et al. "Basis Weight Uniformity of Lightly Needled Hydroentangled Cotton and Cotton Blend Webs." Journal of Engineered Fibers and Fabrics, vol. 1, Issue 1 (2006); pp. 47-61.*

* cited by examiner

PH 100% Cotton

COSMETIC PAD

This is a continuation of Ser. No. 10/514,312 filed Nov. 12, 2004, now abandoned which is the national stage of PCT/EP2003/007629 filed on Jul. 15, 2003 and also claims Paris Convention priority of EP 024 00 033.3 filed on Jul. 15, 2002, the entire disclosures of which are hereby incorporated by reference.

BACKGROUND OF THE INVENTION

The invention concerns a cosmetic pad for cleaning the skin or for removing make-up, as well as for applying cosmetic products such as creams, onto the skin.

There are many different types of cosmetic pads. EP 1 106 723 A1 discloses e.g. a cosmetic pad, both surfaces of which are water-jet needled. The cosmetic pad may also comprise 0 to 30% of artificial fibers, such as viscose fibers, polyester fibers, or bicomponent fibers.

EP 0 836 842 B1 discloses cosmetic pads and the production thereof. The pads comprise hydrophilic materials such as e.g. cotton, viscose or flax and/or hydrophobic materials such as e.g. polyethylene terephtalate or polypropylene. However, cosmetic pads are preferred which consist of 100% cotton, which consist of 100% viscose, which have at least 25% viscose, the rest being cotton, which have at least 25% cotton, the rest being viscose, which have 50% viscose and 50% polyethylene terephtalate, or which have 50% viscose and 50% polypropylene. Water jet solidification is used to solidify the nonwoven fiber material.

EP 0 405 043 B1 discloses a three-layered cosmetic pad, wherein the layers consist of 100% cotton noils. The two outer layers are tightly compacted and have a honeycomb pattern on their respective visible side. The three layers are combined into a sandwich-type construction. The edge regions of at least the outer layers are preferably connected to each other.

In accordance with WO 00/76384 A1, a cosmetic pad consists of 100% cotton fibers, wherein a first layer comprises fine fibers of a thickness of between 0.7 and 1.75 denier (2 to 5 µg/pouce) and a second layer of thicker fibers, which is to form an abrasive surface.

U.S. Pat. No. 4,100,324 describes a fiber mixture of wood pulp fibers and thermoplastic microfibers having an average fiber diameter of less than 10 µm. Due to the fact that this fiber mixture is produced quasi simultaneously with spinning of the microfibers, by e.g. introducing an air flow and a cellulose fiber flow into the region of the spinning head for the microfibers, the fibers are connected and the microfibers cause fixation of the cellulose fibers i.e. in a state in which the microfibers are still at increased temperatures and not yet hardened. The microfibers therefore form matrices for the wood pulp fibers and the wood pulp fibers are embedded in a flexible i.e. not rigid manner, even with very small microfiber contents up to less than 1 weight %. Further fibers or particulate material, including synthetic fibers such as nylon fibers and natural fibers such as cotton, flax, jute, and silk may also be used.

U.S. Pat. No. 4,426,417 describes a nonwoven material formed of a meltblown web of matrix forming fibers with a diameter of up to about 10 µm and incorporated therein a stable fiber mixture including staple synthetic fibers and (staple) cotton fibers. The cotton fibers have a denier of 1-1.5 and the staple synthetic fibers are disclosed having a denier of 15, 6 and 3, respectively.

Due to the production of the fiber mixture quasi in situ with formation of the microfibers in the melt blown process, the microfibers lose their independence in the fiber product and are changed due to contact with the wood pulp fibers in the still molten state.

It is the object of the present invention to produce a cosmetic pad which feels very soft and still has a very high cleaning or make-up removing capability.

SUMMARY OF THE INVENTION

This object is achieved in accordance with the invention with a cosmetic pad comprising or consisting essentially of synthetic micro staple fibers of at least 7 mm in length. The cosmetic pad contains 15 to 85% by weight of micro staple fibers and 15 to 72 weight % cotton fibers.

The term micro staple fibers used above means synthetic fibers having a fiber thickness of $\leq 1$ dtex. The term micro staple fibers means that microfibers of a certain length or in a certain length range which are previously formed in a separate production method and are subsequently used for the production of the nonwoven fiber material layer of the cosmetic pad. It has turned out that synthetic micro staple fibers can make the cosmetic pad softer and therefore provide excellent haptic effect for the user. Surprisingly, this is not associated with reduced cleaning or make-up removing effect. On the contrary, the inventive cosmetic pads having or consisting essentially of synthetic micro staple fibers of a length of at least 7 mm have superior cleaning and make-up removing properties. This may be due to the large surface area produced by the fine structure of the micro staple fibers which can come into contact with the skin surface to be cleaned. This large surface area therefore also defines a large number of micro gaps and openings which may receive impurities, skin particles or make-up.

The fiber length of the micro staple fibers which can be used is preferably 10-38 mm, in particular 15-32 mm. The micro staple fibers can be present in an amount ranging from 15 to 85% by weight, 15-65% by weight or 20-30% by weight.

In a further design of the invention, the micro staple fibers may be polyester (PES) or viscose fibers. The surface of the micro staple fibers is preferably rendered hydrophilic. One of the surfaces of the cosmetic pad may have an imprinted pattern. In this case, the imprinted pattern can be generated in a conventional manner, e.g. through calender imprint or through water jet needling as disclosed in EP-1106723-A2 or WO-99/25318-A1. Generation of the imprinted pattern can be accompanied by solidification of the nonwoven material. The nonwoven material can be solidified by adding thermally melting binding fibers or through the addition of chemical binders, such as e.g. aqueous polymer dispersions, e.g. polyacrylate, polyvinyl acetate, polyvinyl alcohols, latices or binders on the basis of solvents or polyurethanes or powder adhesives/fusion adhesive powder e.g. of polyamide, polyethylene, ethylene vinyl acetate, polyurethane or polyester.

"Hydrophilic" denotes fibers or the surfaces of fibers which are wetted by aqueous liquids in contact with the fibers. The degree of wetting of the materials can be described in terms of contact angles and the surface tensions of the liquids and materials involved. Equipment and techniques suitable for measuring the wettability of particular fiber materials can be provided by conventional commercially available devices. When measured with such systems, fibers having contact angles When measured with such systems, fibers having contact angles less than 90° are designated "wettable" or hydrophilic, while fibers having contact angles equal to or greater than 90° are designated "nonwettable" or hydrophobic.

The surface of the micro staple fibers can be rendered hydrophilic, e.g. by treatment with a surfactant, such as a non-ionic, anionic or amphoteric surfactant, e.g. by spraying the fiber with a surfactant, by dipping the fiber into a surfactant or by including the surfactant as part of the polymer melt when producing the thermoplastic fiber.

The weight per unit area of the inventive cosmetic pad is preferably between 40 and 300 $g/m^2$, in particular 60 to 250 $g/m^2$, preferably 120-250 $g/m^2$, and particularly preferred 150 to 250 $g/m^2$.

For applications in which the cosmetic pad is designed to absorb liquid, i.e. if it should be suitable to receive a skin-cleaning solution or for removing make-up using a make-up removing means having a high liquid portion, the cosmetic pad advantageously also includes up to 72 weight % of cotton fibers, in particular 15 to 65 weight % and also in particular 50 to 65 weight % of cotton fibers. Cotton comber noils are preferably used. Those cotton comber noils are obtained from standard yarn production where the machine separates long from short cotton fibers. The short fibers are separated from the yarn production as cotton comber noils. The cosmetic pad may comprise cotton fibers which are treated with a softener of at least 0.2 weight %. This softener may comprise a fatty acid condensation product and/or functional polydimethyl siloxanes and/or polyethylenes.

In order to obtain a high internal stability for the inventive cosmetic pad, it is also particularly preferred to additionally include thermally melting binding fibers, preferably in an amount of 10-20 weight %, and to thermally solidify the cosmetic pad with these binding fibers. The portion of thermally melting binding fibers relative to the mass of the cosmetic pad is, in particular, 12-18 weight % and more preferred 12-15 weight In a further design of the invention, the binding fibers may be multi-component fibers, in particular, bicomponent fibers having a carrier component which melts at higher temperatures and a component which melts at lower temperatures.

The multi-component fibers, in particular bi-component fibers preferably have a fiber thickness of 1.3-10 dtex, in particular 1.3-3.0 dtex and a fiber length of 3 to 60 mm. Core/jacket fibers or side-to-side fibers are preferably used.

The use of bicomponent fibers having a copolyester (CO-PES) as the low melting component and polyester (PES) as the component with the higher melting temperature has proven to be advantageous.

The melting point of the thermally melting binding fibers or of the low melting component (e.g. CO-PES) of the multi-component fibers is lower than the melting point of the micro staple fibers, as is of particular importance in a further design of the invention. Micro staple fibers from a polyester material could e.g. be used having a melting point of approximately 256° C. and CO-PES/PES bicomponent fibers with a melting point for the low melting component CO-PES of 110° C. and for the higher melting component PES of 255° C. In this case, thermal solidification of the nonwoven fiber material could be carried out without thermally changing the higher melting component of the bicomponent fibers and the micro staple fibers.

In a further development of the invention, one side of the cosmetic pad has a rough surface effected by applying an abrasive in the form of a coating. This produces a cosmetic pad having one side which is experienced as being very soft and has a very high cleaning effect as explained above, and one rough side which is used for "peeling", i.e. for removing dead skin particles while also providing a pleasant massaging effect.

The abrasive may preferably be formed from a thermoplastic fusion adhesive powder. The fusion adhesive powder may be disposed as a powdery component, e.g. using a precision distributor via a vibrating screen, onto one side of the cosmetic pad and be thermally fixed at that location. Thermal fixation is preferably effected by sintering in an oven. The fusion adhesive powder does not thereby melt, rather the particles are connected to the cosmetic pad by the sintering process while maintaining their particle shape to form the rough surface structure. The fusion adhesive preferably used in this case comprises polyethylene and/or polyamide and/or polyester. It has a grain size of 1-500 μm, in particular 1-100 μm, preferably 1-65 μm. It has proven to be useful and advantageous when the abrasive is applied with a weight per unit area of 5-50 $g/m^2$, in particular 10-40 $m^2$ and preferably 15-30 $g/m^2$.

The abrasive powder and the micro staple fiber can be made from the same type of material. However, the materials used must not have the same thermal properties and melting of one material does not necessarily cause melting of the other, despite the fact that they may both be made from the same type of material, e.g. polyester. (For example there are different polyesters having different melting points). The cosmetic pad can have a rough surface effecting by bonding an abrasive onto the pad. The pad can be made by selecting a thermoplastic fusion powder having a melting temperature which differs from a melting temperature of the micro staple fibers, thereby allowing the fusion process to occur without melting the fibers.

In a further development of the invention, the cosmetic pad may be wetted during manufacture and packaged in a damp state in a substantially moisture-proof manner to be sold to the end user in this form. The invention also concerns damp cloths, i.e. damp nonwoven materials of the above-described inventive nonwoven fiber material. Damp and dry cotton swabs can also be produced therefrom.

Damp cosmetic pads or damp cloths also preferably comprise cotton fibers which are or can be treated with a softener of at least 0.2 weight %, in particular of the above-described type. Damp pads are preferably wetted with an oil-in-water cleaning emulsion having a viscosity of <2000 mPas, preferably <800 mPas. The oil-in-water emulsion may comprise a portion of 0.2 to 0.5 weight % of a preservative, e.g. parabene or benzyl alcohols. 2-5 weight % of plant extracts and 0.2 to 0.5 weight % of perfume oil portion may also be contained in the oil-in-water emulsion.

The, in particular, damp cosmetic pads or damp cloths preferably have a low optical permeability of less than 0.9%, preferably less than 0.75%, particularly preferred less than 0.70%, and particularly preferred of less than 0.6%. The optical permeability is measured at a wavelength of 600 nm with a Perkin-Elmer Lambda 2 UV/VIS spectrophotometer on specimens of 30 mm×40 mm in size.

The optical impermeability is an indication for the packed density of the fiber material and therefore a measure of the fiber surface available for cleaning.

In accordance with the invention, the cleaning effect of a cosmetic pad or damp cloth, in particular a damp cosmetic pad, can be determined through measurement of its optical permeability thereby permitting a comparison of the cleaning effect of different cosmetic pads or damp cloths. Independent patent protection is therefore claimed, in particular, for a damp cotton fiber pad or damp fiber cloth having a low optical permeability of less than 0.9%, preferably less than 0.75%, particularly preferred of less than 0.70%, particularly preferred of less than 0.6%, in dependence on the type of fibers used and of the fiber composition.

Damp cloths which are commercially available have optical permeabilities of 1.76% (Nivea Visage, Erfrischende Reinigungstücher für normale Haut und Mischhaut, Beiersdorf AG), 2.26% (Bebe Young Care Quick'n Clean für alle Hauttypen, Johnson & Johnson), 2.57% (Diadermine, Pflegende Reinigungstücher für Gesicht und Augen, für alle Hauttypen, Schwarzkopf und Henkel Laboratories Diadermine), 0.96% (Demak'up Reinigungstücher, 100% Baumwolle, für normale und Mischhaut, Georgia Pacific).

In a preferred embodiment of the inventive damp cloths, the cloths are provided with an emulsion and have an optical permeability of 0.55% (damp cloth 1) or 0.48% (damp cloth 2). The composition of the damp cloths is given below.

Damp cloth 1: 37% PES micro staple fibers with a fiber thickness of 0.9 dtex and a fiber length of 18 mm, 23% cotton noils, 40% viscose fibers with a fiber thickness of 1.7 dtex and a fiber length of 40 mm. The weight per unit area of the dry nonwoven fiber material was 63 g/m$^2$. The thickness of the dry nonwoven fiber material was 0.66 mm, measured at a pressure of 0.5 kPa with a test surface of 25 cm$^2$.

Damp cloth 2: 49% PES micro staple fibers with a fiber thickness of 0.9 dtex and a fiber length of 18 mm and 51% cotton noils. The weight per unit area of the dry nonwoven fiber material was 78 g/m$^2$. The thickness of the dry nonwoven fiber material was 0.80 mm, measured at a pressure of 0.5 kPa with a test surface of 25 cm$^2$.

The damp cloths 1 and 2 were impregnated with Emulgade CM (Cognis Deutschland GmbH & Co.KG, PIT-emulsion), which is an oil in water emulsion consisting of water, cetearyl isononanoat, ceteareth 20, cetearyl alcohol, phenoxy ethanol, parabene, potassium sorbate, glycerin, perfume, citric acid, cetyl palmitate and ceteareth 12 (INCI declaration). The emulsion concentration was 7.5%. The amount of emulsion was 300% referred to the dry weight of the nonwoven fiber material (i.e. 300 g of thinned emulsion to 100 g nonwoven material).

To produce the inventive cosmetic pads, the synthetic micro staple fibers which are produced in a separate process are disposed in a conventional nonwoven material forming method to form a nonwoven material. If different fiber types are used, these are advantageously previously mixed in an air flow and then disposed. If thermally melting binding fibers are present, thermal fixing of the nonwoven material can be performed in an "air-through-method" with a gas temperature which can be accurately adjusted, preferably without thereby thermally influencing or impairing the synthetic micro staple fibers and their structure. In an alternative or also additional manner, water jet needling of the nonwoven fiber material web may be provided before or after thermal fixing. Irrespective thereof, imprint calendering on one or two sides may be used to provide the cosmetic pad with a surface pattern.

The nonwoven material from which the inventive pad is made is a manufactured sheet, web or batt of directionally or randomly oriented fibers, bonded by friction, adhesion, cohesion, but excluding paper and products which are woven, knitted, tufted or stitch-bonded incorporating binding yarns or filaments, or which are felted by wet-milling, whether or not additionally needled. Consolidation may be achieved by conventional means—either alone or in combination—such as needle-punching, water entanglement (=water jet needling=spunlacing), compressing, embossing, calendaring or thermal bonding. Compressing, embossing and calendaring may be preferably combined with thermal bonding. In addition or alternatively, consolidation may also be achieved using binders. Binders may include any conventional binders such as particulates, powders, solvent binders or fibrous binders, preferably in the form of thermally melting binding fibers. Thermal bonding can also be achieved by air-through bonding.

The inventive cosmetic pad is preferably compacted such that it has a longitudinal stability or maximum tensile strength in a longitudinal direction (machine direction) of 5-30 N/25 mm, in particular 10-25 N/25 mm and preferably >15N/25 mm and a maximum tensile strength in a transverse direction (transverse to the machine direction) of 5-30 N/25 mm, in particular 8-20 N/25 mm and preferably >10N/25 mm. In the embodiment of a damp cloth, in particular the longitudinal stability or maximum tensile strength in a longitudinal direction of the damp cloth (machine direction) is advantageously 5-70 N/25 mm, preferably 10-60 N/25 mm, and with particular preference 30-50 N/25 mm and the maximum tensile strength in a transverse direction (transverse to the machine direction) is advantageously 5-60N/25 mm, in particular 10-50N/25 mm and preferably 20-40N/25 mm. This maximum tensile strength may be determined using a standardized tensile testing machine in accordance with DIN 5122 using the following testing method: Samples having a clamping width of 25 mm and a clamping length of 30 mm are taken from the cosmetic pad to be examined, i.e. from a central region. The samples are clamped vertically in the clamping receptacles of the standardized tensile testing machine which are moved apart with a testing speed of 100 mm/min at the plane of their extension to thereby measure the tensile force acting in this direction. The maximum tensile force is the force at which the cosmetic pad is torn. If previously higher force peaks were measured during expansion, these represent the maximum tensile force in the sense of this procedure. For measurements in the longitudinal and transverse directions which corresponds to the machine direction or a direction transverse thereto, different, in particular five individual measurements can be taken and their average value can be calculated.

The inventive cosmetic pad preferably has a thickness of preferably 0.5 to 4.5 mm which is determined at a specific measuring pressure of 0.5 kPa on a 25 cm$^2$ surface of a specimen sample. The testing method corresponds to DIN EN ISO 9073-2 (testing method for nonwoven materials, determination of the thickness).

The absorptive capacity of inventive cosmetic pads can also be determined. Corresponding to PH.EUR.1997, Monografie Verbandwatte aus Baumwolle, a test of the absorptive capacity is determined by measuring the sinking time in a liquid of a wire basket filled with specimens to be tested. The wire basket which can be used in this case is a cylindrical basket of copper wire with a wire diameter of 0.4 mm. The height is 80 mm, the diameter 50 mm, the mesh width 15-20 mm and the mass 2.7+/−0.3 g. Moreover, a beaker of a diameter of 11-12 cm is used. The cosmetic pads to be tested are put into the wire basket until a testing amount of 5 g is obtained. The basket is previously weighed with an accuracy of 0.01 g (M1). The 5 g of specimen material constitute a mass M2. The beaker is filled with demineralized water to a level of approximately 100 mm and the filled basket is dropped onto the water from a height of 10 mm. The time needed to sink below the surface is measured with a stop watch. Directly after determination of the sinking time, the basket is lifted out of the water and is horizontally held along its longitudinal axis for 30 s of dripping time. After lapse of the dripping time, the basket is put into a counterbalanced beaker (M3) and weighed with an accuracy of 0.01 g (M4).

The water retaining capacity is given by:

$$g/g = \frac{M4 - (M2 + M3)}{M2 - M1}$$

The sinking time and the water retaining capacity are given as an average value of three measurements. The sinking time of preferred cosmetic pads is maximally 15 sec and the water retaining capacity is at least 10 g/g. This can be adjusted through the portion of absorbing fibers and/or through the addition of hydrophiliation agents.

Further features, details and advantages of the invention can be extracted from the following claims and the figure and the following description of one preferred embodiment of the invention.

DESCRIPTION OF THE PREFERRED EMBODIMENT

Two preferred compositions of the inventive cosmetic pads are shown below: They are indicated with PH and PH*.

| Fiber type | PH | PH* |
| --- | --- | --- |
| Micro staple fibers PES | 25 weight % | 47 weight % |
| Cotton comber noils | 62 weight % | 40 weight % |
| Bicomponent fibers CO-PES/PES | 13 weight % | 13 weight % |

The cosmetic pads PH and PH* were obtained by mixing previously produced micro staple fibers having a fiber thickness of 0.9 dtex and a fiber length of approximately 18 mm with cotton comber noils and the bicomponent fibers in an air flow in the respective weight percentage compositions. The micro staple fibers are polyester fibers with a melting point of 256° C. The bicomponent fibers are core jacket fibers with a polyester core component having a higher melting point of 255° C. and a jacket of a copolyester (CO-PES) with a melting point of 110° C. The length of these bicomponent fibers is 51 mm and their thickness is 1.35 dtex.

These cosmetic pads were compared with comparable products, wherein the following examination of the cleaning and make-up removing effect was carried out: Make-up was disposed on a substrate to determine, under standardized conditions, how the respective cosmetic pads remove make-up from that substrate. Towards this end, a tensile testing machine (DIN 51221, class 1) was used. The substrate was "smooth beige goat leather for the production of shoes". 0.1 g of a protecting cream make-up (Nivea Beauté Teint Natur Intensive) was uniformly deposited onto a piece of this smooth goat leather having a size of 30×100 mm and left to dry for 2 to 2½ hours.

To carry out the examination, circular blotting paper (Schleicher & Schüll, Nr. 860) having a diameter of 57 mm (the same size as the cosmetic pad to be tested which also has a diameter of 57 mm) was punched out and soaked with 0.85-0.9 g demineralized water. The round cosmetic pad (specimen) (diameter 57 mm, 25.5 cm$^2$) is disposed on the soaked blotting paper and loaded for 10 s with 1 kg. The cosmetic pad thereby absorbs some liquid. The cosmetic pad with moistened surface is then disposed on the goat leather in front of the location with "make-up". A cylindrical weight of 300 g, a diameter of 57 mm, and having a lug is connected to the tensile device of the tensile testing machine using a string. The connected weight is fixed using two-sided sticky tape so that it exactly covers the cosmetic pad. The cosmetic pad and the weight are then drawn over the "make-up" surface at a speed of 200 mm/min. At least five make-up removing tests are carried out and the amount of make-up remaining on the goat leather is judged visually or using a color measuring device (chromameter). The above-described cosmetic pads PH and PH* and a cosmetic pad which consists of 100 weight % cotton, PH 100% cotton are used as specimens, wherein the latter is available under the trademark "Labell" and is solidified through water jets. Moreover, a cosmetic pad of the available trademark "Demak'up Duo" and of the trademark "Demak'up Supersoft" were examined which also consist of 100% cotton and is solidified through water jets. Cosmetic pads of the trademarks "Nivea" and "Jean Carol" each consist of 100% cotton and are also water-jet solidified. A cosmetic pad imprinted on both sides (trademark "Hydra") was also tested.

FIGS. 1 through 8 each show visual reproductions of two make-up removing tests, e.g. the image which results if a cosmetic pad was drawn once over the "make-up" surface in the manner described above. The cosmetic pad used in this case was turned and positioned on the substrate at the initial position of the make-up removing test and a visual reproduction was recorded.

One can see that the products PH and PH* achieved a much more effective cleaning action or make-up removing effect compared to the comparable products.

A comparison of the inventive products PH and PH* shows that the increase in the microfiber portion improves the make-up removing effect.

Figure 1:
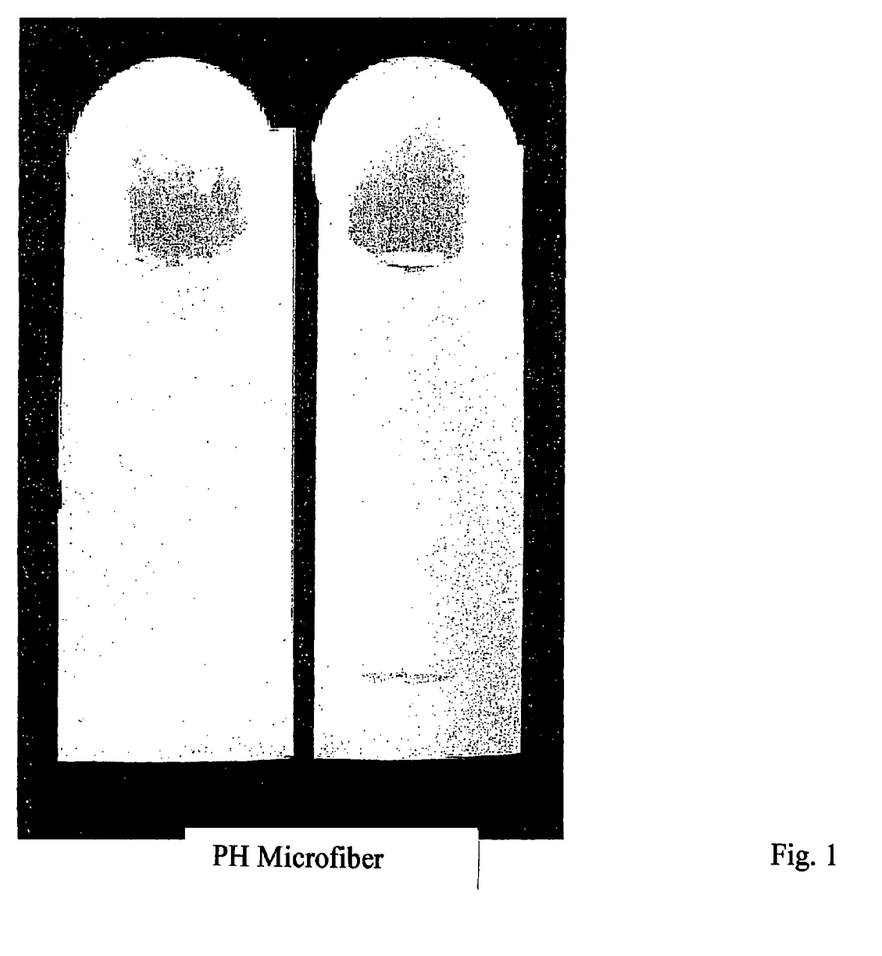
FIG. 1 shows the result of a first experiment for determining the cleaning or make-up removing effect of cosmetic pads.
Figure 2:
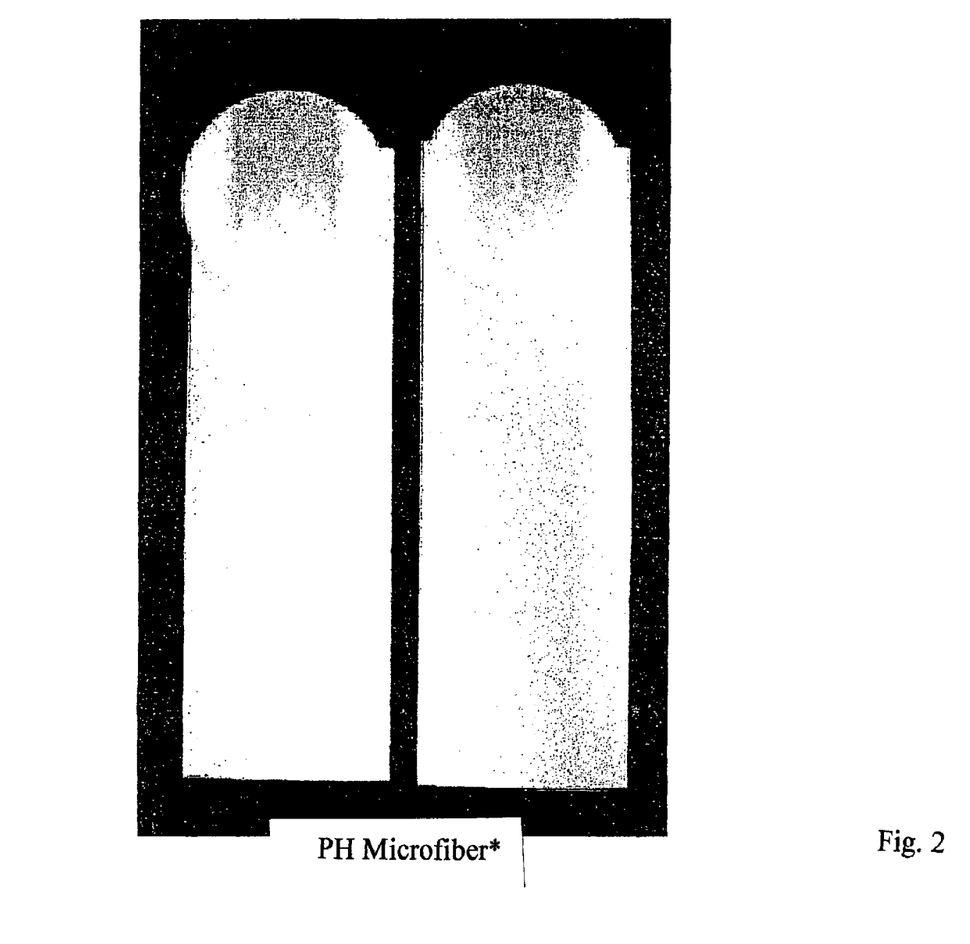
FIG. 2 shows the result of a second experiment for determining the cleaning or make-up removing effect of cosmetic pads.
Figure 3:
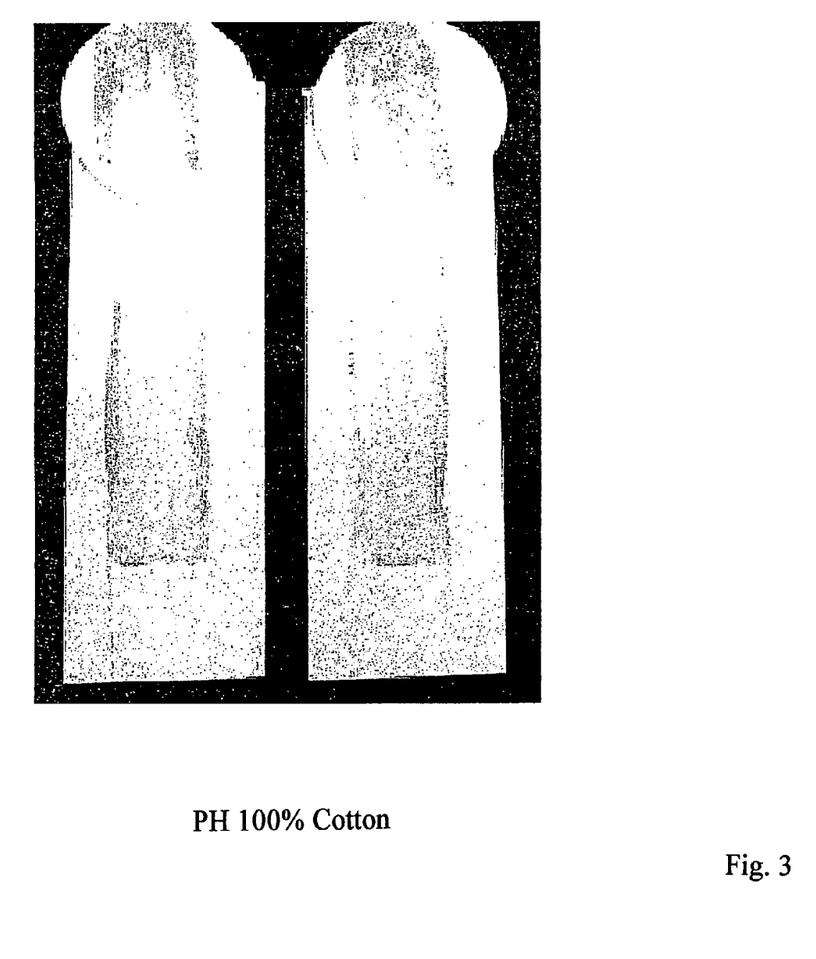
FIG. 3 shows the result of a third experiment for determining the cleaning or make-up removing effect of cosmetic pads.
Figure 4:
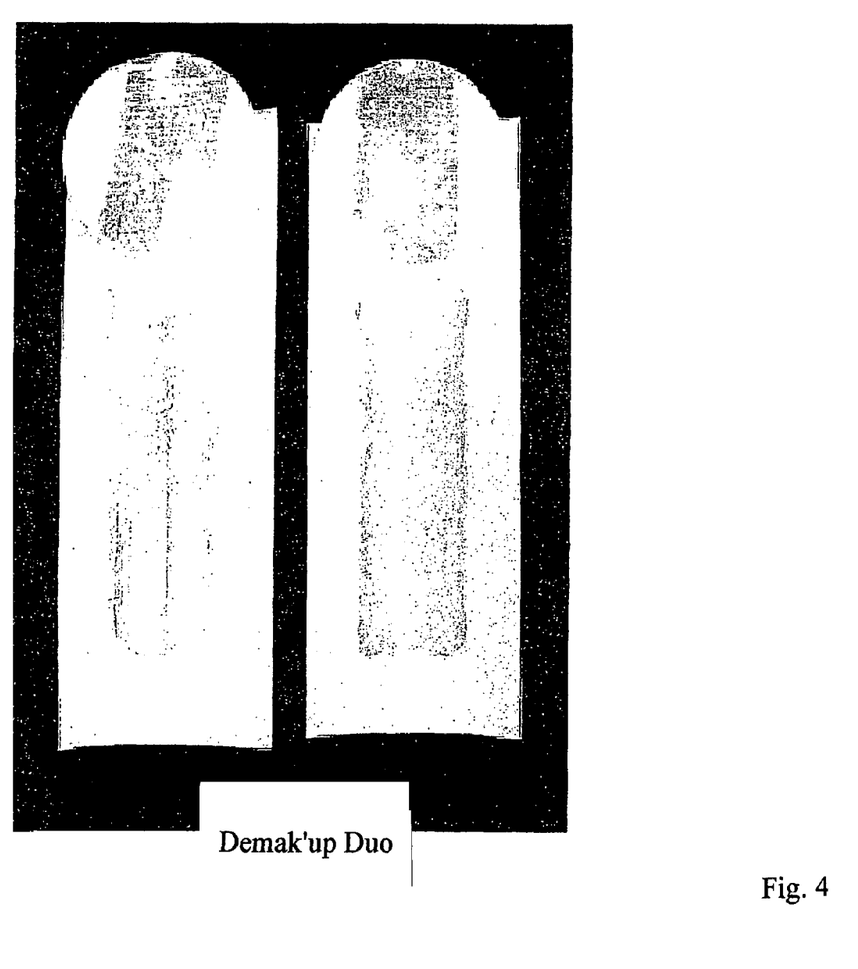
FIG. 4 shows the result of a fourth experiment for determining the cleaning or make-up removing effect of cosmetic pads.
Figure 5:
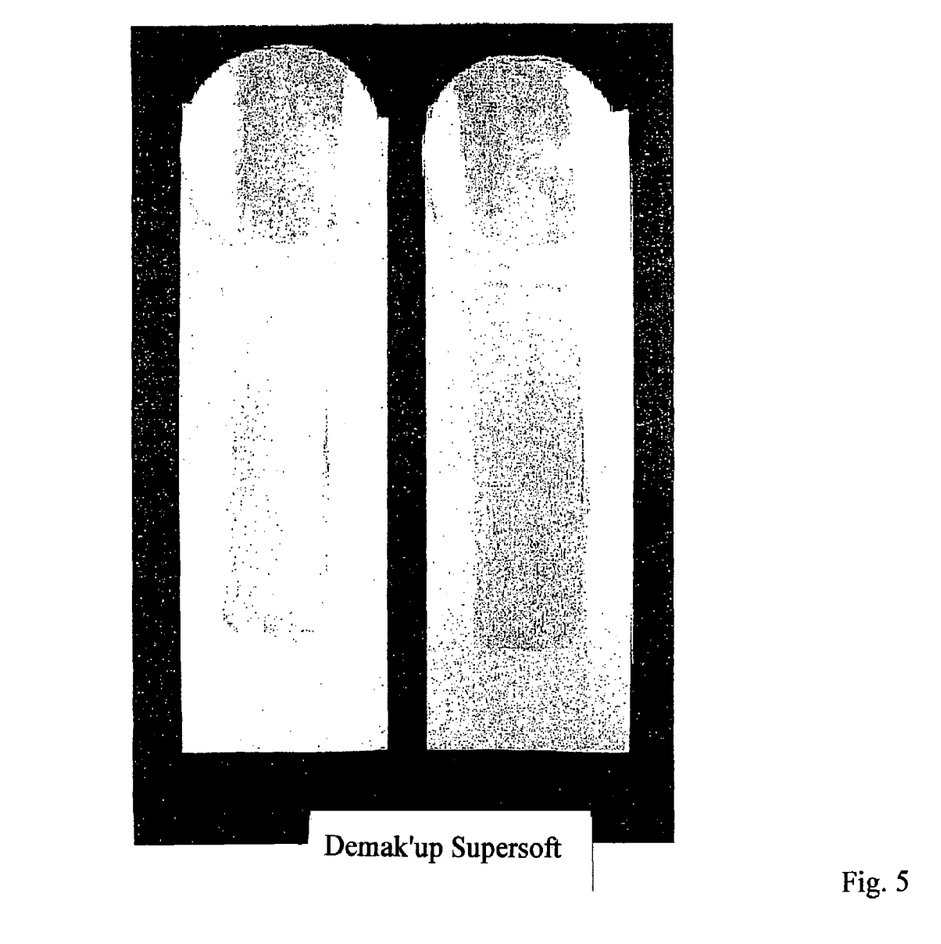
FIG. 5 shows the result of a fifth experiment for determining the cleaning or make-up removing effect of cosmetic pads.
Figure 6:
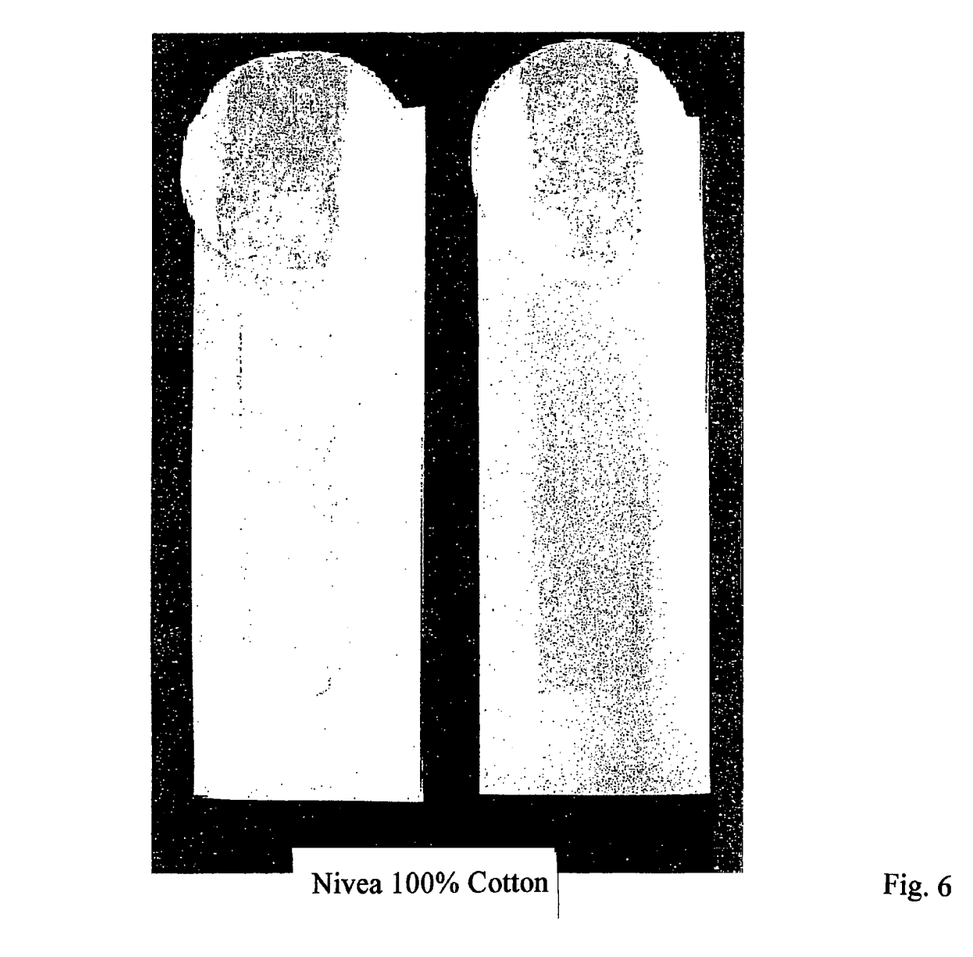
FIG. 6 shows the result of a sixth experiment for determining the cleaning or make-up removing effect of cosmetic pads.
Figure 7:
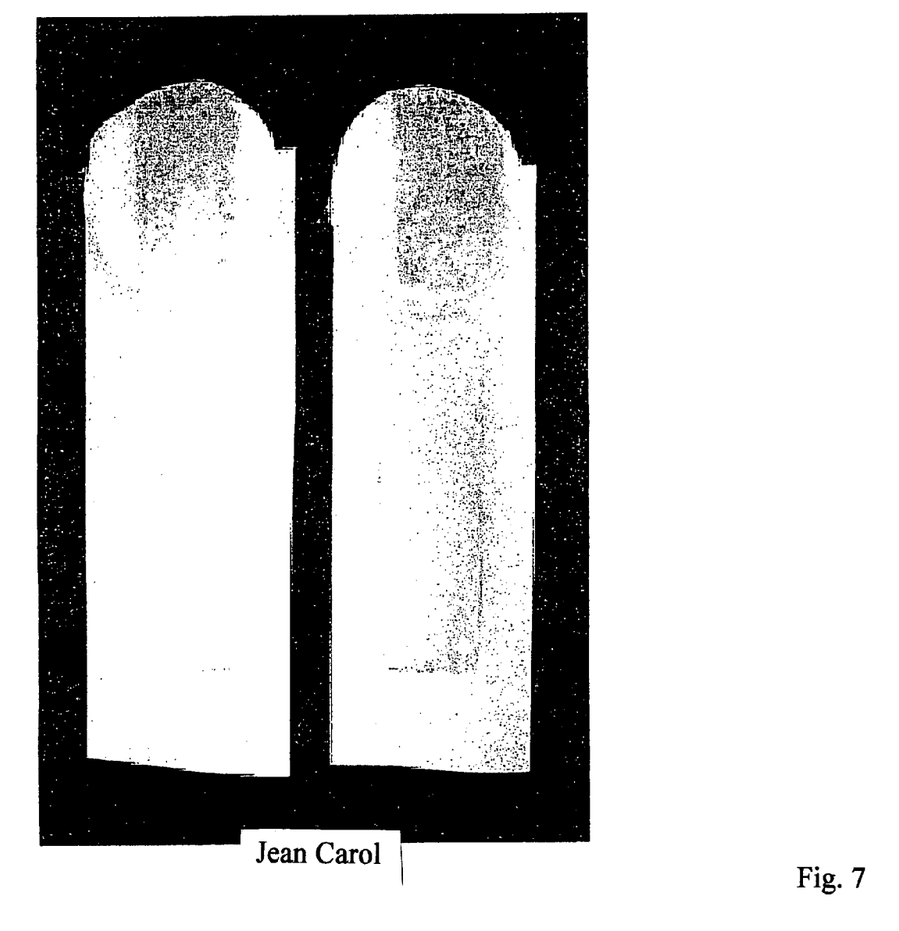
FIG. 7 shows the result of a seventh experiment for determining the cleaning or make-up removing effect of cosmetic pads.
Figure 8:
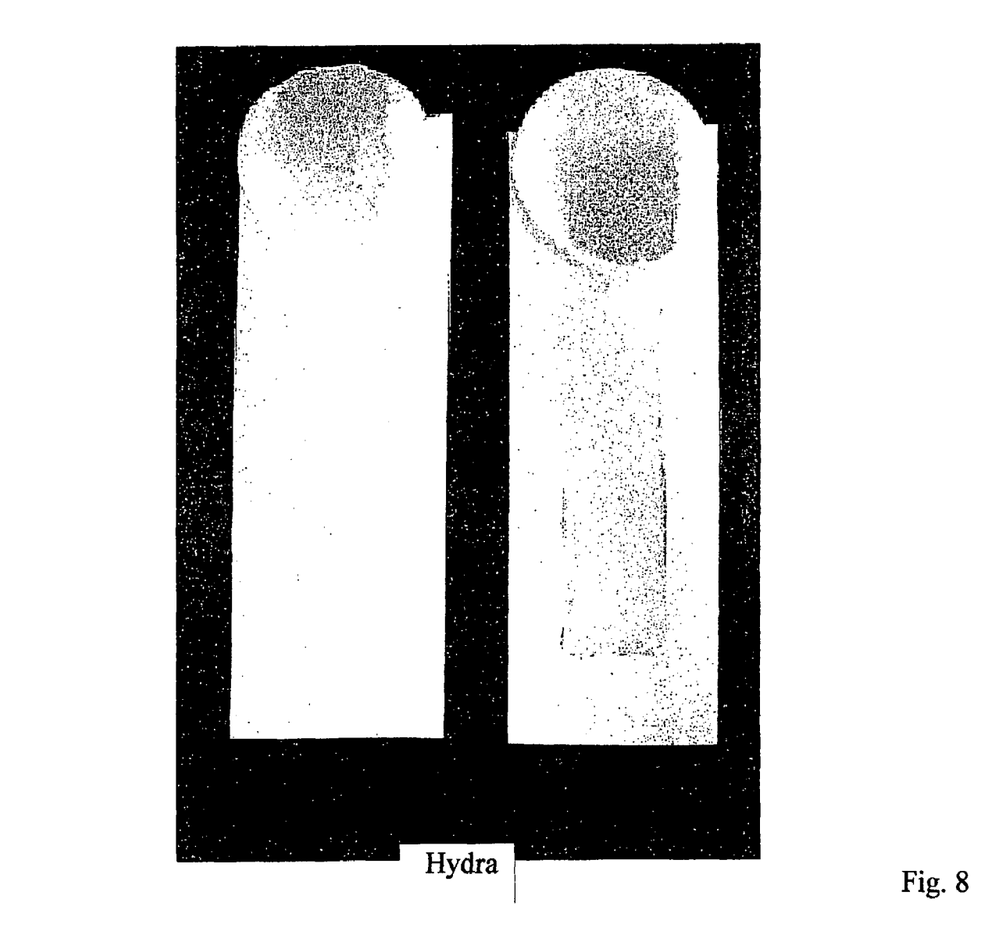
FIG. 8 shows the result of an eighth experiment for determining the cleaning or make-up removing effect of cosmetic pads.
Figure 9:
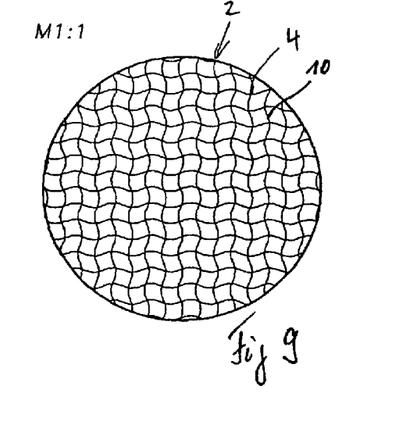
FIG. 9 shows a first surface pattern of a cosmetic pad.
Figure 10:
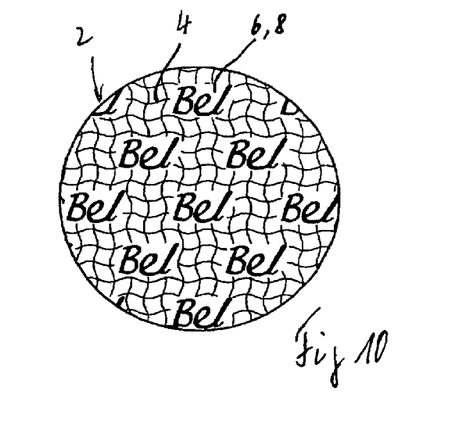
FIG. 10 shows a second surface pattern of a cosmetic pad.
Figure 11:
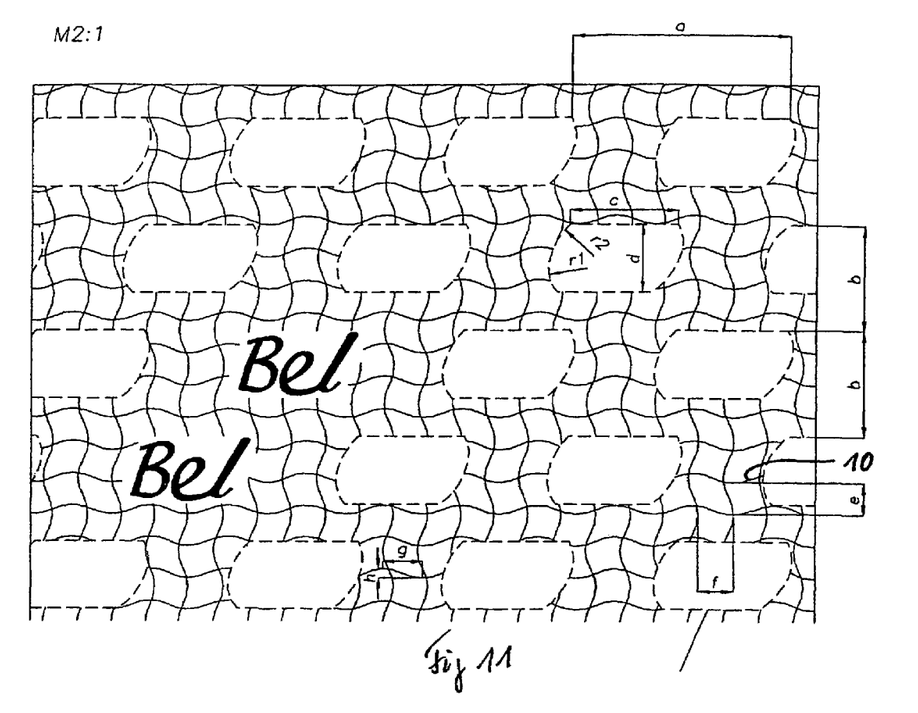
FIG. 11 shows the surface pattern of FIG. 10 in detail.

FIGS. 9 and 10 show two plan views of an inventive cosmetic pad 2 with different imprinted patterns 4 generated through imprint calendering of the disposed cosmetic pad. The depth of the grooves of the imprint pattern 4 is at least 0.4 mm. FIG. 11 shows details of the imprint pattern. It comprises a honeycomb or waffle-like structure which is interrupted by a second imprint pattern 6 in the form of letters 8. The separations between the honeycomb lines 10 are between 2.0 and 5 mm, in particular between 2.5 and 4.0 mm. The second imprint pattern 6 has an area of up to 15×10 mm (dimensions c×d). The separation between the regions receiving the respectively second imprint pattern 6 is 3-10 mm (dimension b–d), in particular 4-6 mm in one direction or 5-15 mm (dimension a–c), in particular 8-12 mm in the other direction.

The imprint lines 10 forming the honeycombs and the imprint pattern 4 are wavy having a half wavelength g of 2-8 mm, in particular 3-5 mm and a wavelength height h of 0.5-2 mm, in particular 0.8-1.2 mm.

We claim:

1. A cosmetic pad comprising a nonwoven material consisting of:
    15 to 85% by weight of micro staple fibers selected from the group consisting of synthetic micro staple fibers of at least 7 mm in length and having a fiber thickness of <1 dtex and viscose micro staple fibers of at least 7 mm in length and having a fiber thickness of <1 dtex, and
    15 to 72% by weight of cotton fibers and
    10 to 20% by weight of thermally melting binding fibers being multi-component fibers or bi-component fibers and having a fiber thickness of 1.3 to 10 dtex and a fiber length of 3 to 60 mm,
    wherein these different fiber types being mixed in an airflow and then disposed to form the nonwoven material, where the micro staple fibers are previously formed in a separate production method and subsequently used to be mixed in an airflow with the cotton fibers and the thermally melting binding fibers and then disposed to form the cosmetic pad,
    the cosmetic pad having a tensile strength of 5 to 30 N/25 mm in a machine direction and in the embodiment of a wetted cosmetic pad or damp cloth having a tensile strength of 5 to 70 N/25 mm in a machine direction.

2. The cosmetic pad of claim 1, wherein said micro staple fibers are polyester (PES) fibers.

3. The cosmetic pad of claim 1, wherein the surface of said micro staple fibers is rendered hydrophilic.

4. The cosmetic pad of claim 1, wherein a weight per unit area of the pad is 40-300 g/m$^2$, 60-250 g/m$^2$, 120-250 g/m$^2$, or 150-250 g/m$^2$.

5. The cosmetic pad of claim 1, wherein a portion of micro staple fibers is 15-65 weight % or 20-30 weight %.

6. The cosmetic pad of claim 1, wherein said cotton fibers have a weight percentage portion of up to 15-65 weight %, or 50-65 weight %.

7. The cosmetic pad of claim 6, wherein the cotton fibers are cotton comber noils.

8. The cosmetic pad of claim 1, wherein said thermally melting binding fibers have a weight percentage portion of 12-18 weight %, or of 12-15 weight %.

9. The cosmetic pad of claim 1, wherein said multi-component fibers have a fiber thickness of 1.3 to 3.0 dtex.

10. The cosmetic pad of claim 1, wherein said bicomponent fibers are copolyester (CO-PES)/polyester (PES) bicomponent fibers.

11. The cosmetic pad of claim 1, wherein a melting point of said thermally melting binding fiber is lower than the melting point of said micro staple fibers.

12. The cosmetic pad of claim 1, wherein a melting point of a low melting component of said multi-component fibers is lower than a melting point of said micro staple fibers.

13. The cosmetic pad of claim 1, wherein one side of the pad has a rough surface effected by bonding an abrasive onto the pad.

14. The cosmetic pad of claim 13, wherein said abrasive is formed from a thermoplastic fusion adhesive powder which is sintered onto one side of the pad.

15. The cosmetic pad of claim 14, wherein said fusion adhesive powder comprises polyethylene, polyamide and/or polyester.

16. The cosmetic pad of claim 14, wherein said abrasive or said fusion adhesive powder has a grain size of 1-500 μm, 1-100 μm, or 1-65 μm.

17. The cosmetic pad of claim 13, wherein said abrasive is disposed with a weight per unit area of 5-50 g/m$^2$, or 10-40 g/m$^2$, or 15-30 g/m$^2$.

18. The cosmetic pad of claim 1, wherein the pad is wet during manufacture and packaged in a damp state in a substantially moisture-proof fashion.

19. The cosmetic pad of claim 1, further comprising cotton fibers which are treated with a softener to at least 0.2 weight %.

20. The cosmetic pad of claim 19, wherein said softener comprises a fatty acid condensation product, functional polydimethyl siloxanes, and/or polyethylenes.

21. The cosmetic pad of claim 18, wherein the pad is wet with an oil-in-water emulsion having a viscosity of <2000 mPas, or of <800 mPas.

22. The cosmetic pad of claim 21, wherein said oil-in-water emulsion comprises a preservative, parabene, or benzyl alcohol in an amount of 0.2-0.5 weight %.

23. The cosmetic pad of claim 1, wherein the pad has an optical permeability of less than 0.9%, less than 0.75%, less than 0.70%, or less than 0.6%.

24. A method for using the cosmetic pad of claim 1, the method comprising the step of:
    rubbing the cosmetic pad against a users skin to remove make-up or to clean the skin.

* * * * *